US008355563B2

(12) United States Patent
Kasahara et al.

(10) Patent No.: US 8,355,563 B2
(45) Date of Patent: Jan. 15, 2013

(54) PHOTOVOLTAIC DEVICES INSPECTION APPARATUS AND METHOD OF DETERMINING DEFECTS IN PHOTOVOLTAIC DEVICE

(75) Inventors: Masato Kasahara, Hamamatsu (JP); Toshio Shibuya, Okazaki (JP)

(73) Assignee: Nisshinbo Holdings Inc., Tokyo (JP)

( * ) Notice: Subject to any disclaimer, the term of this patent is extended or adjusted under 35 U.S.C. 154(b) by 786 days.

(21) Appl. No.: 12/495,553

(22) Filed: Jun. 30, 2009

(65) Prior Publication Data
US 2010/0002932 A1 Jan. 7, 2010

(30) Foreign Application Priority Data
Jul. 1, 2008 (JP) .................................. 2008-171925

(51) Int. Cl.
*G06K 9/00* (2006.01)
(52) U.S. Cl. ........................................ 382/149; 382/141
(58) Field of Classification Search .......................... None
See application file for complete search history.

(56) References Cited

U.S. PATENT DOCUMENTS

| 2008/0088829 | A1* | 4/2008 | Fuyuki ........................... 356/230 |
| 2009/0127448 | A1 | 5/2009 | Fuyuki |
| 2009/0238444 | A1* | 9/2009 | Su et al. ........................ 382/149 |

FOREIGN PATENT DOCUMENTS

| EP | 1 840 541 A1 | 10/2007 |
| JP | 02-031175 A | 2/1990 |
| JP | 04-106460 A | 4/1992 |
| JP | 06-097508 A | 4/1994 |
| JP | 2007-88419 A | 4/2007 |
| JP | 2007-088419 A | 4/2007 |
| JP | 2008-026113 A | 2/2008 |
| JP | 2008-26113 A | 2/2008 |
| WO | 2006/059615 A1 | 6/2006 |
| WO | 2006059615 A1 | 6/2006 |
| WO | 2007/129585 A1 | 11/2007 |
| WO | 2007129585 A1 | 11/2007 |

OTHER PUBLICATIONS

XP-001109755, Light Emission As a Solar Cell Analysis Technique, Christiana Honsberg and Aleen M. Barnett (Oct. 12, 1986).
Photographic surveying of minority carrier diffusion length in polycrystalline silicon solar cells by electroluminescence, Takashi Fuyuki, Hayato Kondo, Tsutomu Yamazaki, Yu Takahashi, and Yukiharu Uraoka, Applied Physics Letters 86, 262108 (2005).

* cited by examiner

*Primary Examiner* — Paul Danneman
(74) *Attorney, Agent, or Firm* — Apex Juris, pllc; Tracy M. Heims

(57) ABSTRACT

A photovoltaic devices inspection apparatus and method of determining defects in photovoltaic devices that uses electroluminescence can find both the quality of the photovoltaic devices from the state of electroluminescence and the possibility of the photovoltaic devices becoming defective in the future by applying constant electric current to the photovoltaic devices causing electroluminescence of the photovoltaic devices (S7), photographing the light emitted from each photovoltaic cell of the photovoltaic devices (S10), dividing the photographed image of the photovoltaic cell into a bright region and dark region by using a threshold value and displayed as an enhanced image by binarization, analyzing as classifying each photovoltaic cell defect according to defect types and comparing a shape of the dark region with the defect types (S50), determining the existence of the defect to perform a positive-negative quality judgment on the photovoltaic devices, and displaying images of the problematic regions for visual inspection (S16).

18 Claims, 13 Drawing Sheets

FIG. 5
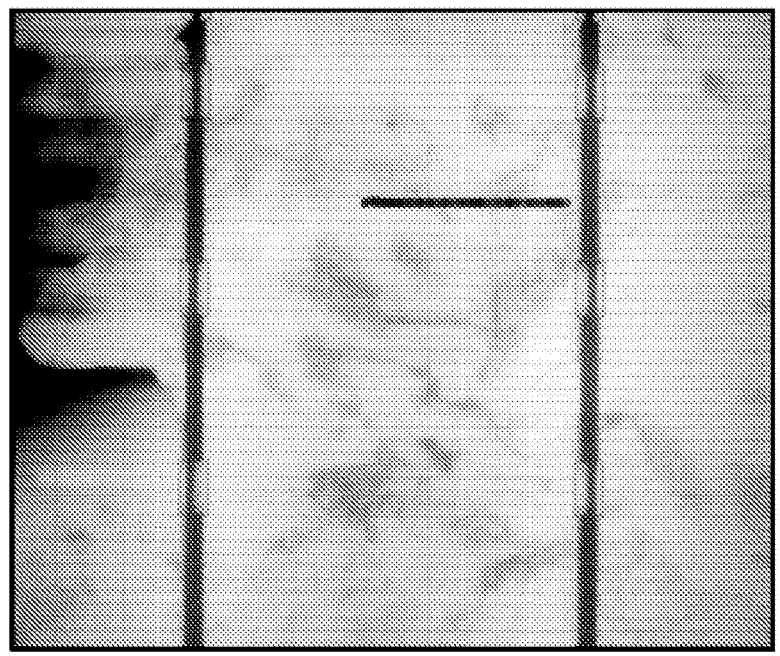
(a) PHOTOGRAPHED (ORIGINAL) IMAGE
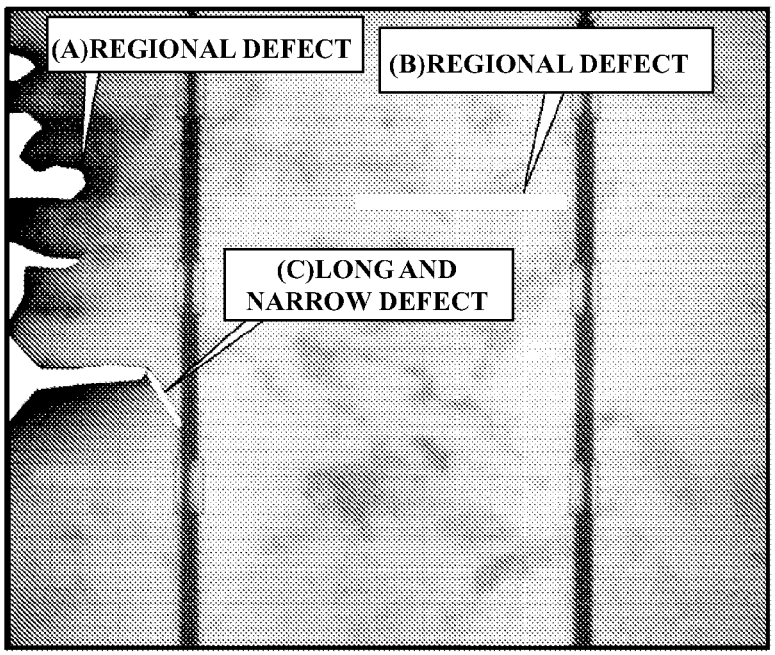
(b) DETERMINED (PROCESSED) IMAGE

EXAMPLE OF EL IMAGE OF
POLYCRYSTALLINE SILICON CELL

θ: ANGLE OF BENT PART

PHOTOVOLTAIC DEVICES INSPECTION APPARATUS AND METHOD OF DETERMINING DEFECTS IN PHOTOVOLTAIC DEVICE

CLAIM FOR PRIORITY

The present specification claims priority from Japanese Patent Application No. 2008-171925, filed on Jul. 1, 2008 in the Japan Patent Office, the entire contents of which are hereby incorporated by reference herein.

BACKGROUND OF THE INVENTION

1. Field of the Invention

The present invention relates to photovoltaic devices inspection apparatus configured to inspect a photovoltaic device that includes at least one photovoltaic cell and a method of determining defects in photovoltaic devices.

2. Description of the Background Art

It is well known that silicon photovoltaic devices are employed to harness solar energy. In the manufacture of photovoltaic devices it is important to evaluate whether the photovoltaic devices have predetermined power generation capacity. The evaluation is usually performed by measuring the output characteristics thereof.

The output characteristics are photovoltaic conversion characteristics evaluated by measuring the current-voltage characteristics of the photovoltaic devices under light irradiation. As a light source, it is desirable to use solar light. However, since the intensity of the solar light varies with weather, a solar simulator is employed. In the solar simulator, a xenon lamp, a metal halide lamp or the like is employed as an alternative to solar light. If the aforementioned light source has been lit for a long time, the temperature thereof rises, leading to a variation on the light intensity thereof. Based on data collected using flash light of such a lamp, the output characteristic curves of the photovoltaic devices can be plotted by designating voltage as the horizontal axis and current as the vertical axis, and if the output characteristics of the photovoltaic devices are equal to or higher than reference values, the photovoltaic devices are determined to be non-defective (for example, refer to Patent Document 1).

Another method different from the above-described method using a solar simulator is disclosed in Patent Document 2. In this method, a voltage is applied to a polycrystalline silicon photovoltaic cell in a forward direction so as to generate a forward current and thus emit electroluminescence light (hereinafter referred to simply as "EL light"), and it is determined from the state of the EL light whether the photovoltaic cell is defective or non-defective. By inspecting the EL light emitted from the photovoltaic cell, the current density distribution of the photovoltaic cell can be obtained, and the non-luminescent parts of the photovoltaic cell detected from the unevenness of the current density distribution are determined as defective parts. In addition, if the amount of light emission measured from a photovoltaic cell reaches a predetermined value, the photovoltaic cell is determined to be non-defective, and if the value is not reached, the photovoltaic cell is determined to be defective.

In the method of Patent Document 2, however, the determination of whether a photovoltaic cell passes or not is based only on the brightness of light emitted from the photovoltaic cell; for example, even a photovoltaic cell has a large crack it can be determined to be non-defective if the brightness of light emitted from the photovoltaic cell is equal to or greater than a predetermined value. However, since a photovoltaic cell having a large crack may greatly reduce the performance of photovoltaic devices in the future, such a photovoltaic cell should be determined to be defective.

In Patent Document 3, defects of a photovoltaic device are classified into external defects caused by external factors such as a substrate crack, an electrode fracture, or a loose contact; and internal defects caused by physical properties of a substrate such as a crystalline defect, a transition, or a grain boundary. In addition, a technique is proposed for easily detecting external defects by considering the fact that internal defects are temperature-dependent. According to the technique, when light emitted from a photovoltaic device is observed, the photovoltaic device is heated to weaken internal defects and thus can easily detect external defects.

Patent Document 1: JP-2007-88419-A
Patent Document 2: WO/2006/059615
Patent Document 3: WO/2007/129585

SUMMARY OF THE INVENTION

It is desirable to inspect photovoltaic devices in a production line. However, according to the method disclosed in Patent Document 3, photovoltaic devices cannot be inspected in a production line because it takes much time to change the temperature of the photovoltaic devices.

Accordingly, an object of the present invention is to provide a photovoltaic devices inspection apparatus and a method of determining defects in photovoltaic devices, which can be used to exactly determine defects by the EL emission status which is caused by applying a predetermined current to photovoltaic devices for electroluminescence (EL) emission of the photovoltaic devices. In addition, according to the apparatus and method, photovoltaic devices can be inspected in a production line in a short time.

To achieve these objects, the photovoltaic device inspection apparatus of the present invention has the following characteristic configuration.

1. The photovoltaic devices inspection apparatus is configured to determine whether a photovoltaic cell of photovoltaic devices is defective or non-defective, the photovoltaic devices inspection apparatus comprising: a power supply configured to apply a current to a photovoltaic cell as an inspection-object; a camera configured to photograph the photovoltaic cell when the photovoltaic cell emits light in response to a current applied from the power supply; and an analyzer configured to analyze an image photographed from the photovoltaic cell by using the camera, wherein the analyzer: (a) calculates a threshold value of brightness and darkness based on an average brightness of a region of the photographed image where bright and dark parts are mixed in respect to the photographed image of the photovoltaic cell by using the camera, (b) divides the photographed image into bright and dark regions based on the threshold value of brightness and darkness and displays the bright and dark regions, (c) determines existence of a defect and a defect type for each photovoltaic cell of the photovoltaic device by previously classifying and registering the defect types and comparing a shape of the dark region with the preregistered threshold value of the defect type, (d) enhances the bright and dark regions by binarizing and displaying the bright and dark regions, and (e) determines existence of a defect for each photovoltaic cell of the photovoltaic devices.

2. The analyzer may (a) calculate and determine a threshold value of brightness and darkness where the threshold value of brightness and darkness is a predetermined degree darker than the average brightness of a predetermined small section of the photographed image where bright and dark parts are mixed in respect to the photographed image of the photovoltaic cell, (b) divide the photographed image into bright and dark regions per said small section based on the threshold value of brightness and darkness, (c) enhance the bright and dark regions by binarizing and displaying the bright and dark regions, and (d) determine existence of a defect for each photovoltaic cell of the photovoltaic devices.

3. The analyzer may determine existence of a particular defect only for a predetermined region of the photovoltaic cell and may not determine existence of the particular defect for the other region of the photovoltaic cell.

4. The photovoltaic devices inspection apparatus may further include a display means configured to display an image visibly by binarizing the region determined as an existence of the particular defect and the other region.

5. The region determined as a defect may be displayed on the display means in a state that the region is overlapped with the photographed image.

6. The region determined as a defect may be displayed with a color according to a type of the defect.

7. The camera may consecutively photograph a plurality of photovoltaic cells, and the analyzer may determine whether the adjacent photovoltaic cells are properly arranged based on photographed images of the photovoltaic cells.

In addition, to provide the above-described objects, the photovoltaic devices defect inspection method of the present invention has the following characteristic configuration.

8. The method includes: steps of applying a current from a power supply to a photovoltaic cell of photovoltaic devices as an inspection-object; photographing emitting light from each photovoltaic cell by using a camera when the photovoltaic cell emits light in response to the applied current; and calculating a threshold value based on an average brightness of a region of the photographed image where bright and dark parts are mixed in respect to the photographed image of the photovoltaic cell by using the photographing means; and a dividing the photographed image into bright and dark regions based on the threshold value of brightness and darkness, enhancing the bright and dark regions by binarizing and displaying the bright and dark regions, and determining existence of a defect for each photovoltaic cell of the camera.

9. The analyzer may determine existence of a defect and type of a defect by previously classifying and registering the defect types and comparing a shape of the dark region with the registered defect types, and the analyzer may enhance a region determined as a defect by binarizing and displaying the region determined as a defect and the other region.

10. Existence of a particular defect may be determined only for a predetermined region of the photovoltaic cell, and the existence of the particular defect may not be determined for the other region of the photovoltaic cell.

11. Plural photovoltaic cells may be consecutively photographed, and may be determined whether the adjacent photovoltaic cells are properly arranged based on photographed images of the photovoltaic cells.

12. The region determined as a defect and the other region may be binarized and displayed visibly as an image.

13. The image formed by binarizing the region determined as a defect and the other region may be displayed together with the photographed image of the photovoltaic cell.

Other features and advantages of the present invention will be apparent from the following description when taken in conjunction with the accompanying drawings, in which like reference characters designate similar or identical parts throughout the several views thereof.

According to the photovoltaic devices inspection apparatus and the method of determining a defect of a photovoltaic devices of the present invention, bright and dark regions of a photographed cell image are displayed by enhancing the bright and dark regions through binarization, so that the bright and dark regions can be simply distinguished, and whether the bright and dark regions are defective can be easily and accurately determined.

Furthermore, photovoltaic device defects are classified into several types, and a region suspected to be a defect is compared with stored defect types, so that exact defect determination is possible. In addition, since a shape or size threshold value can be changed according to the defect types, defect determination can be performed according to actual situations. In addition, since it can be determined whether a defect grows or not according to the type of the defect in the future, a potential defect as well as a current defect can be determined. Therefore, photovoltaic devices having improved quality and durability can be provided.

In addition, particular types of defects, such as small cracks, are easily formed in the vicinity of busbars of a photovoltaic cell and may not be problematic in other regions of the photovoltaic cell. Such types of defects can also be appropriately detected according to the present invention. For example, in the case of detecting small cracks at a position distant from a busbar as well as a position adjacent to the busbar, a non-defective dark region caused by a boundary of crystals can be detected as a crack. Therefore, it is desirable that detection of a small crack is not performed for a region distant from a busbar.

By displaying an image enhanced by binarizing defective and non-defective regions of the image, defect determination can be manually performed by viewing. In the case where defective regions are displayed overlapping with a photographed image, the eligibility of defect determination can be confirmed and corrected by viewing the resultant image. Furthermore, defect determination can be properly performed while checking the types of defects by displaying defective regions with different colors according to the types of defects.

BRIEF DESCRIPTION OF THE DRAWINGS

FIG. 2A is a plan view, FIG. 2B is a front view, and FIG. 2C is a right side view.

FIGS. 5A and 5B illustrate exemplary images of a photovoltaic cell of the embodiment, where FIG. 5A illustrates a photographed image, and FIG. 5B illustrates the photographed image in overlap with the image of enhanced defects.

DESCRIPTION OF THE PREFERRED EMBODIMENTS

A detailed description will now be given of illustrative embodiments of the present invention, with reference to the accompanying drawings. In so doing, specific terminology is employed solely for the sake of clarity, and the present disclosure is not to be limited to the specific terminology so selected. It is to be understood that each specific element includes all technical equivalents that operate in a similar manner and achieve a similar result.

Figure 1:
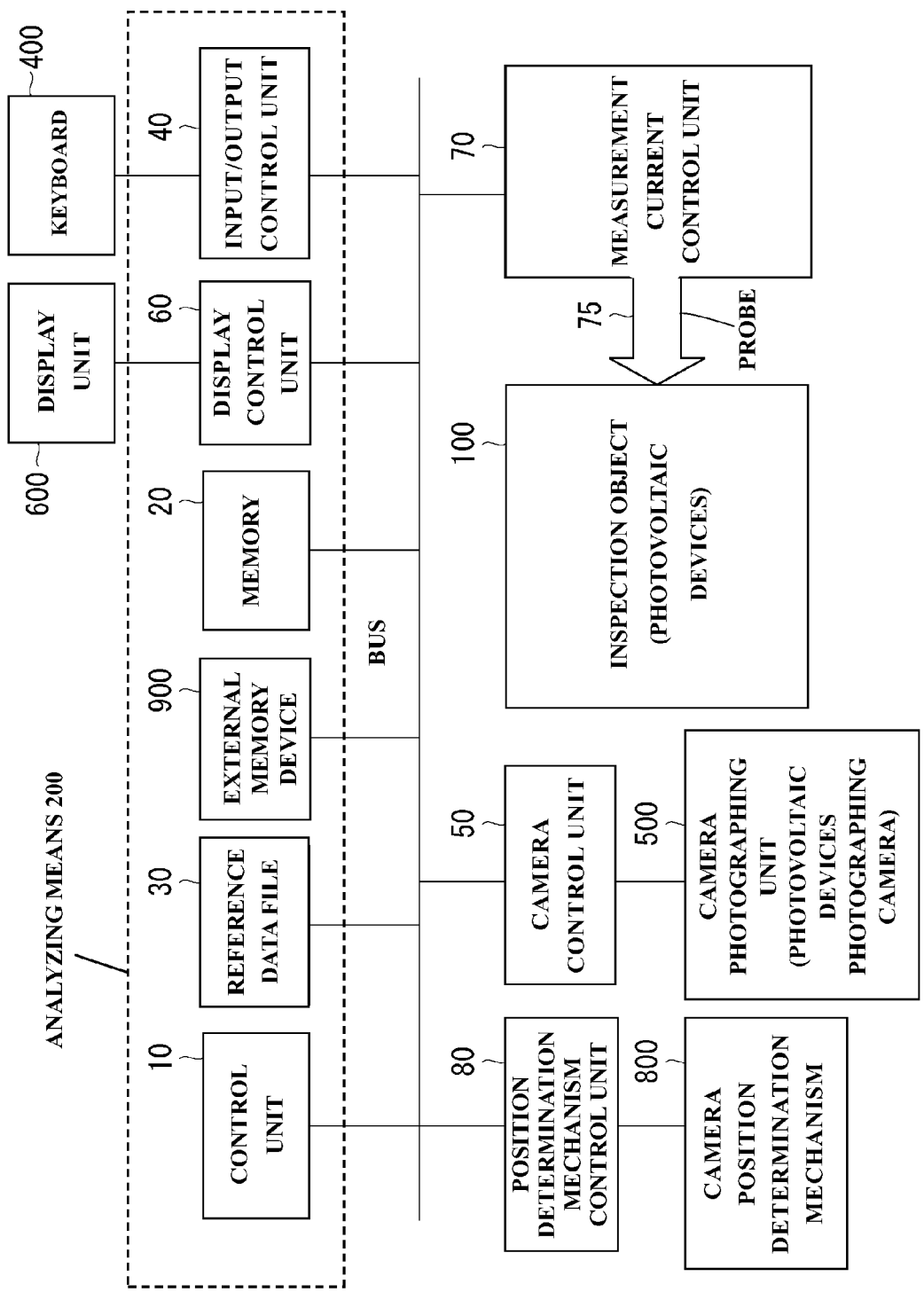
FIG. 1 is a block diagram illustrating a schematic configuration according to an embodiment of the present invention.
Figure 2:
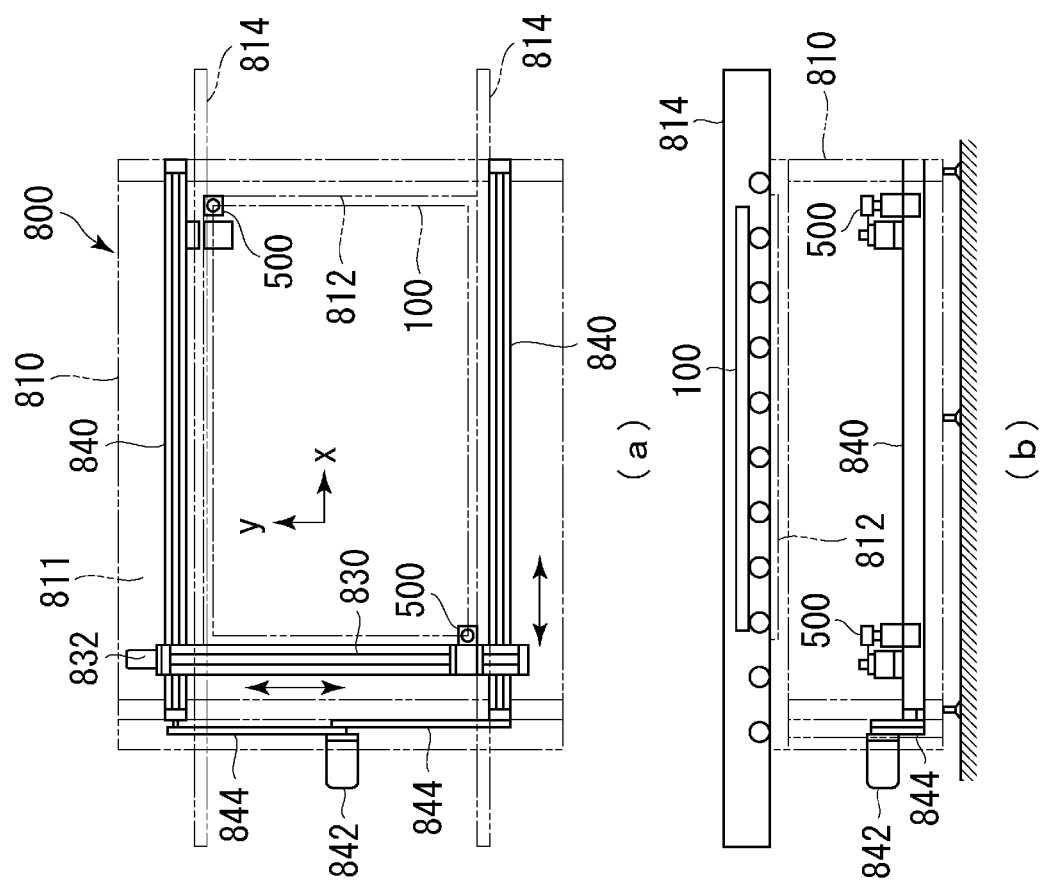
FIGS. 2A to 2C are detailed views illustrating a camera position determination mechanism according to the embodiment of the present invention, where
Figure 3:
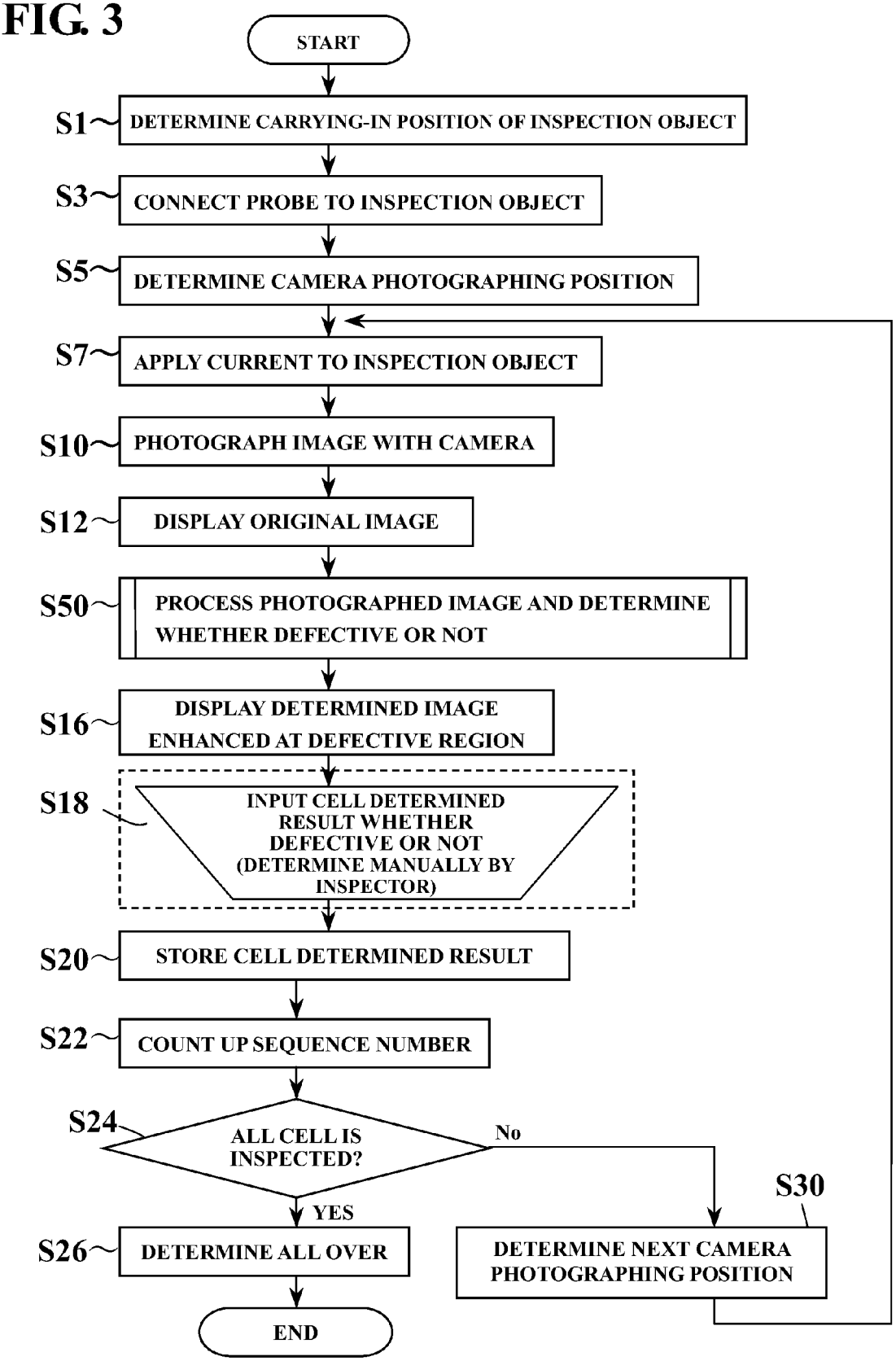
FIG. 3 is a flowchart for explaining a method of inspecting a photovoltaic device according to an embodiment of the present invention.
Figure 4:
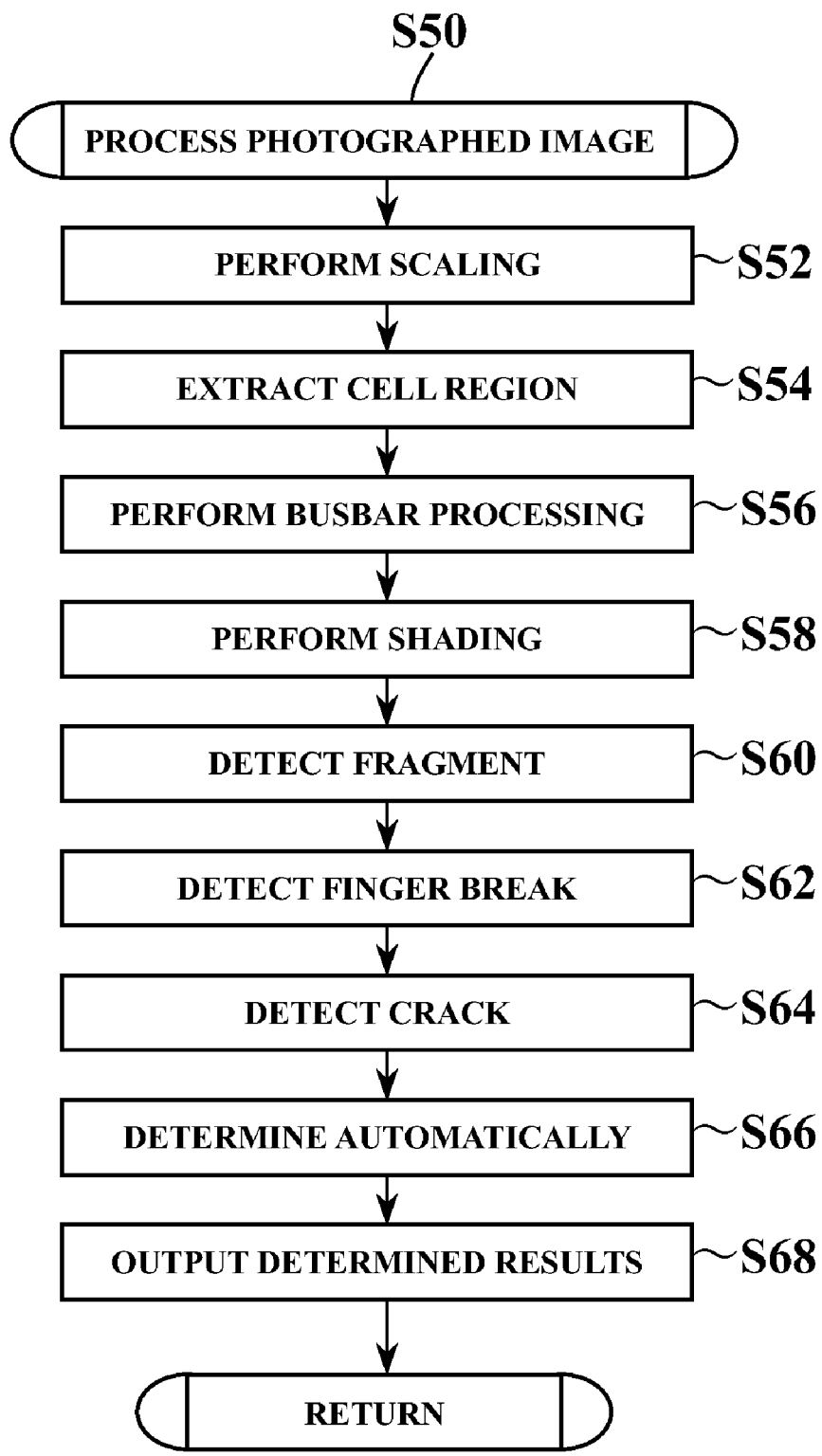
FIG. 4 is a flowchart for specifically explaining the photographed image processing step S50 of FIG. 3.
Figure 6:
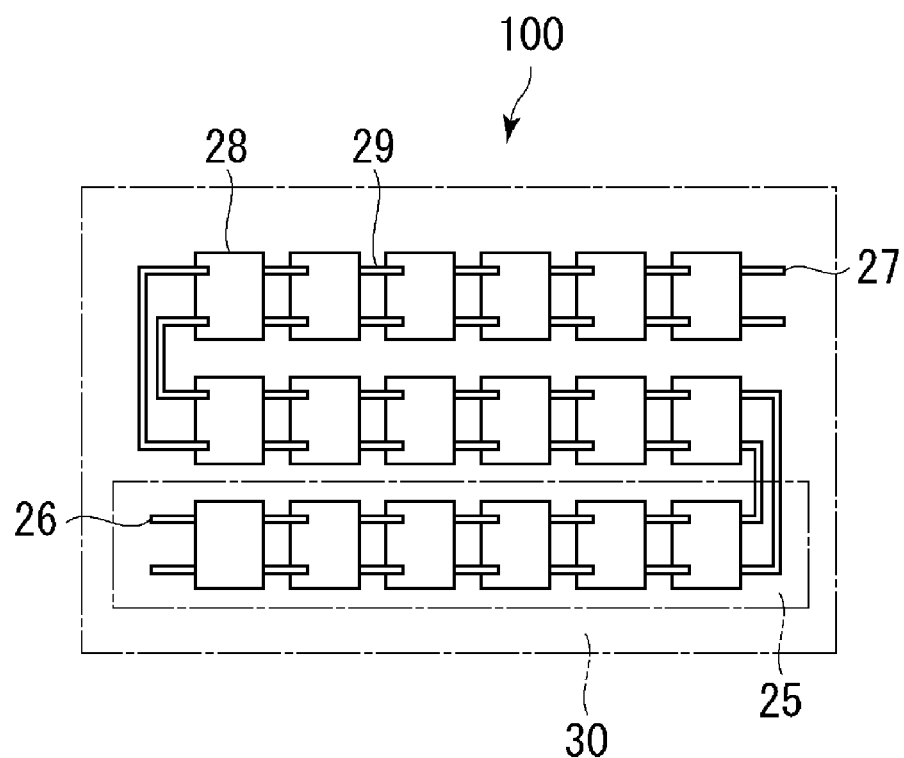
FIG. 6 is a view for explaining photovoltaic cells, strings, and a matrix as an inspection-object.
Figure 7:
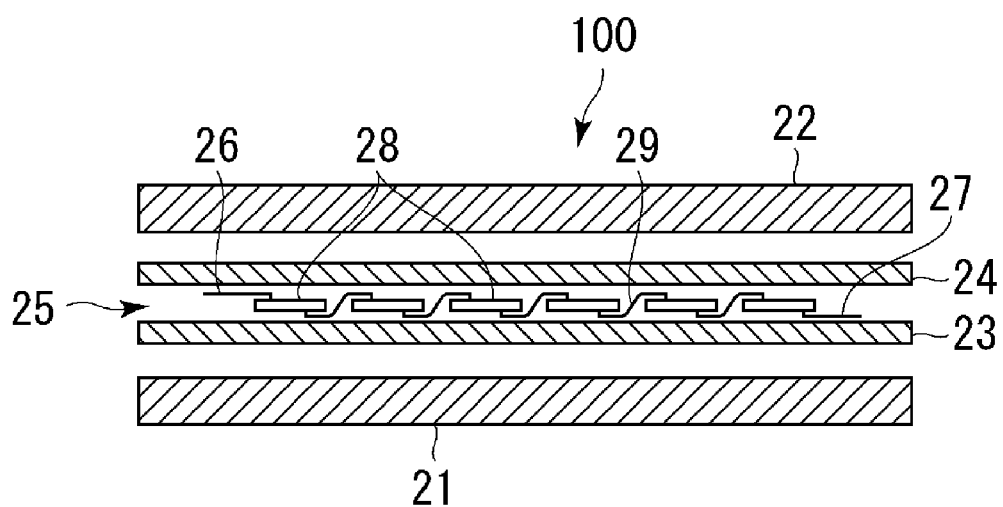
FIG. 7 is a sectional view illustrating the structure of a photovoltaic devices panel as an inspection-object.
Figure 8:
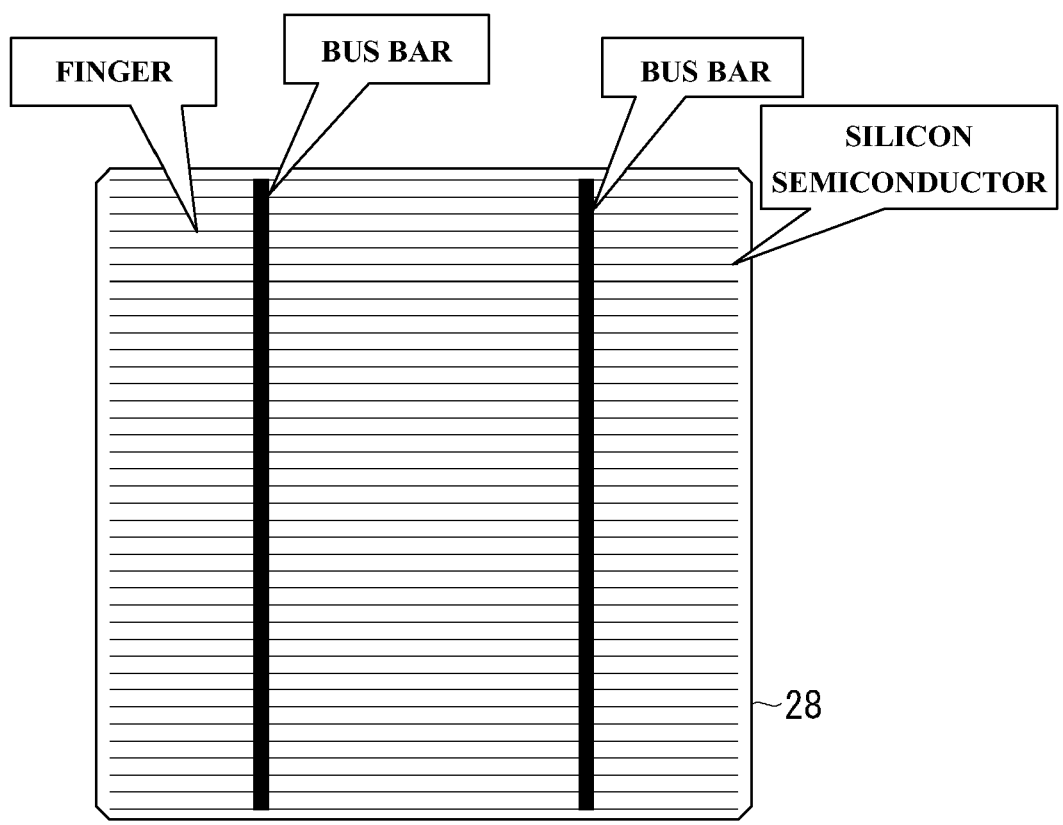
FIG. 8 is a view illustrating a photovoltaic cell as an inspection-object of the inspection apparatus of the present embodiment.
Figure 9:
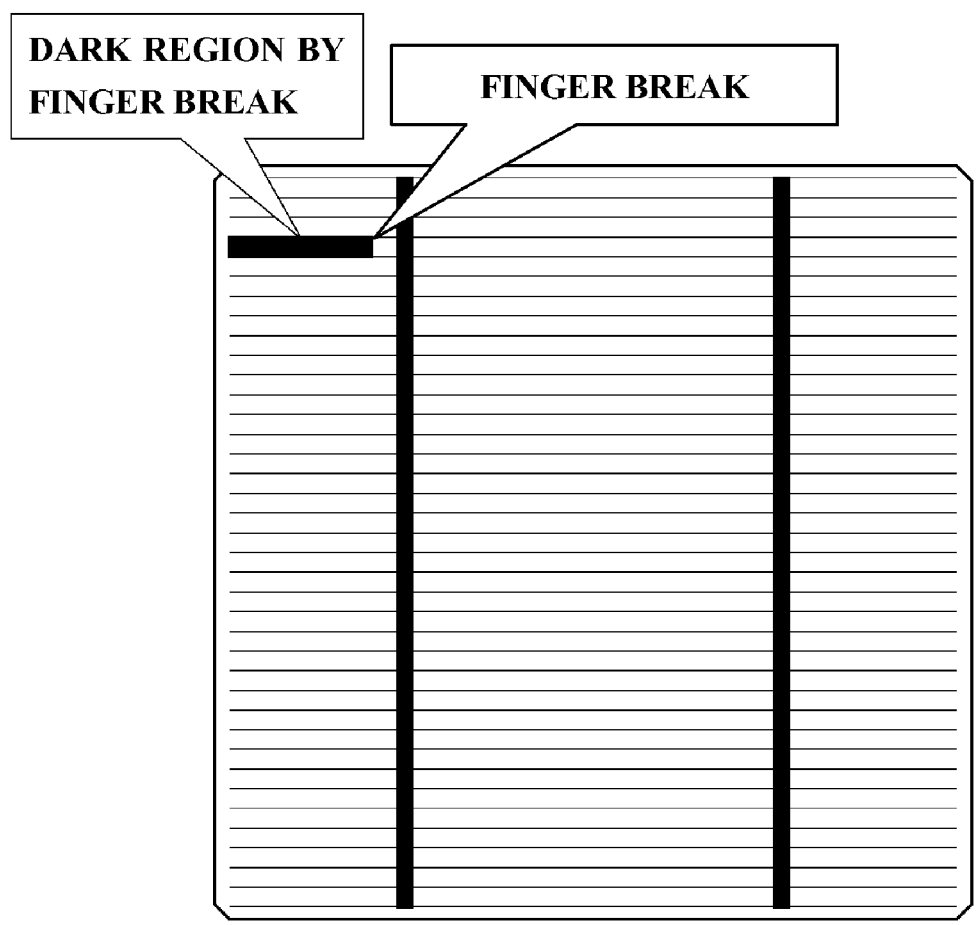
FIG. 9 is a view illustrating an enhanced finger break of a photovoltaic cell in a photovoltaic devices panel as an inspection-object.
Figure 10:
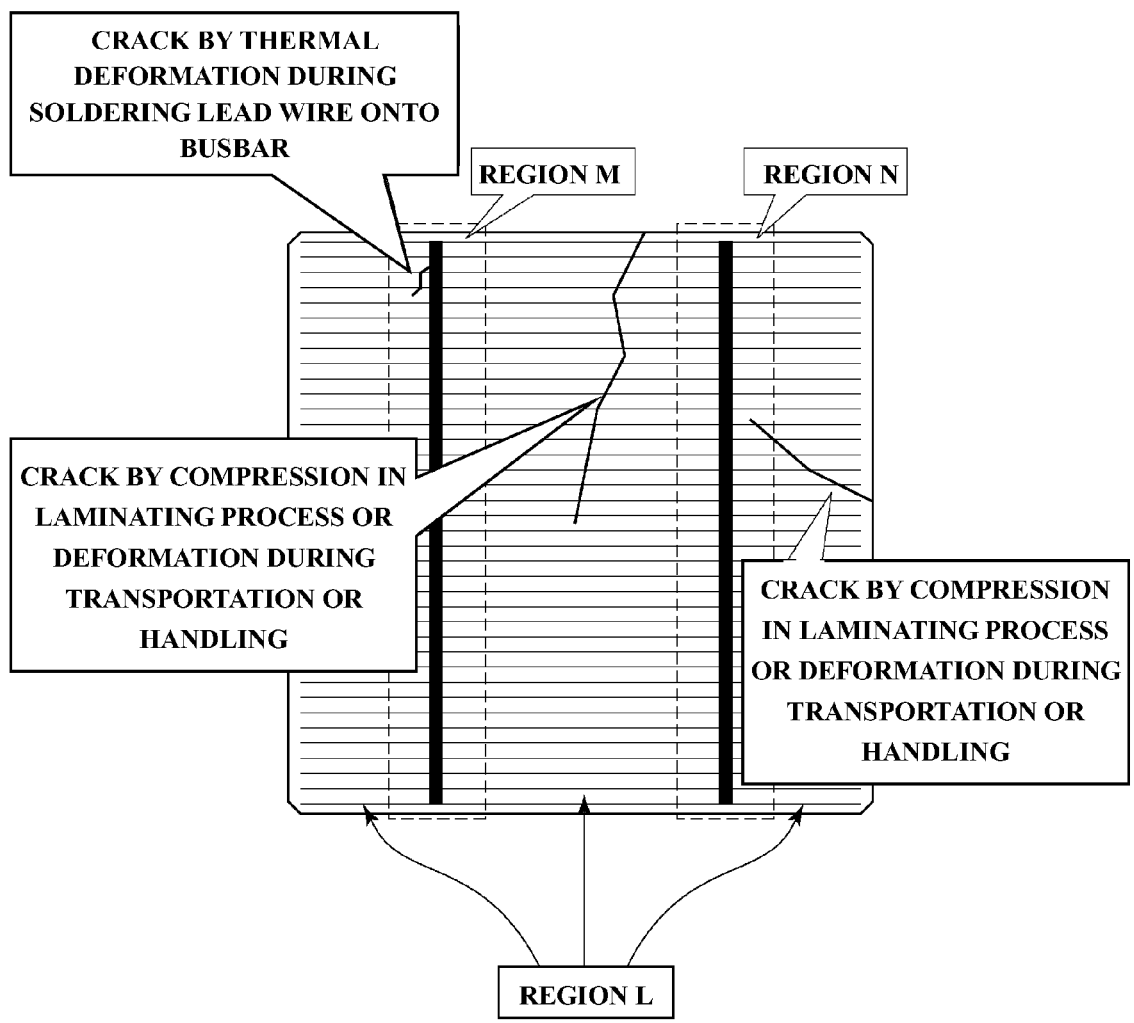
FIG. 10 is a view illustrating enhanced cracks of a photovoltaic cell in a photovoltaic devices panel as an inspection-object.
Figure 11:
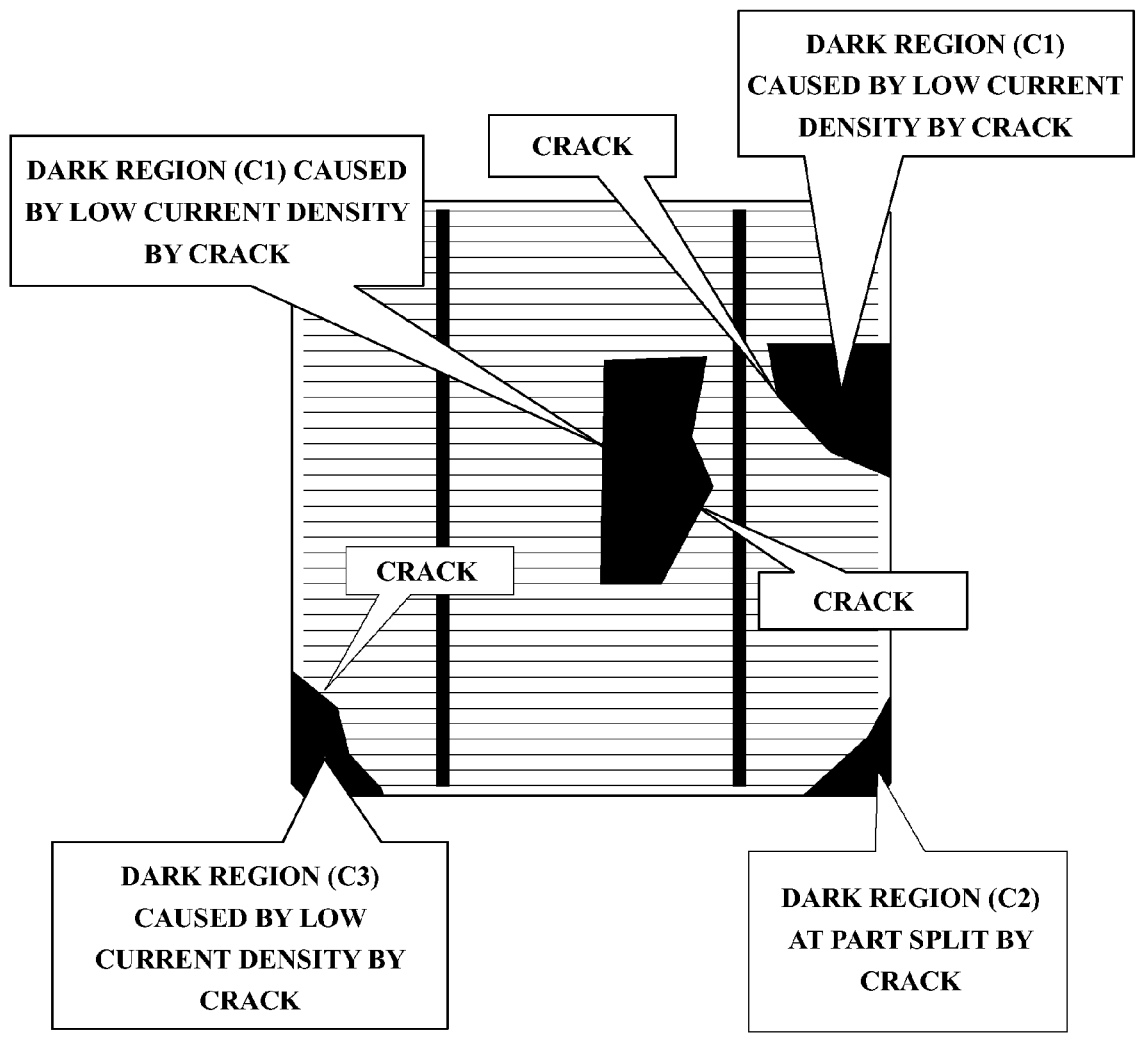
FIG. 11 is a view illustrating enhanced fragment of a photovoltaic cell in a photovoltaic devices panel as an inspection-object.
Figure 12:
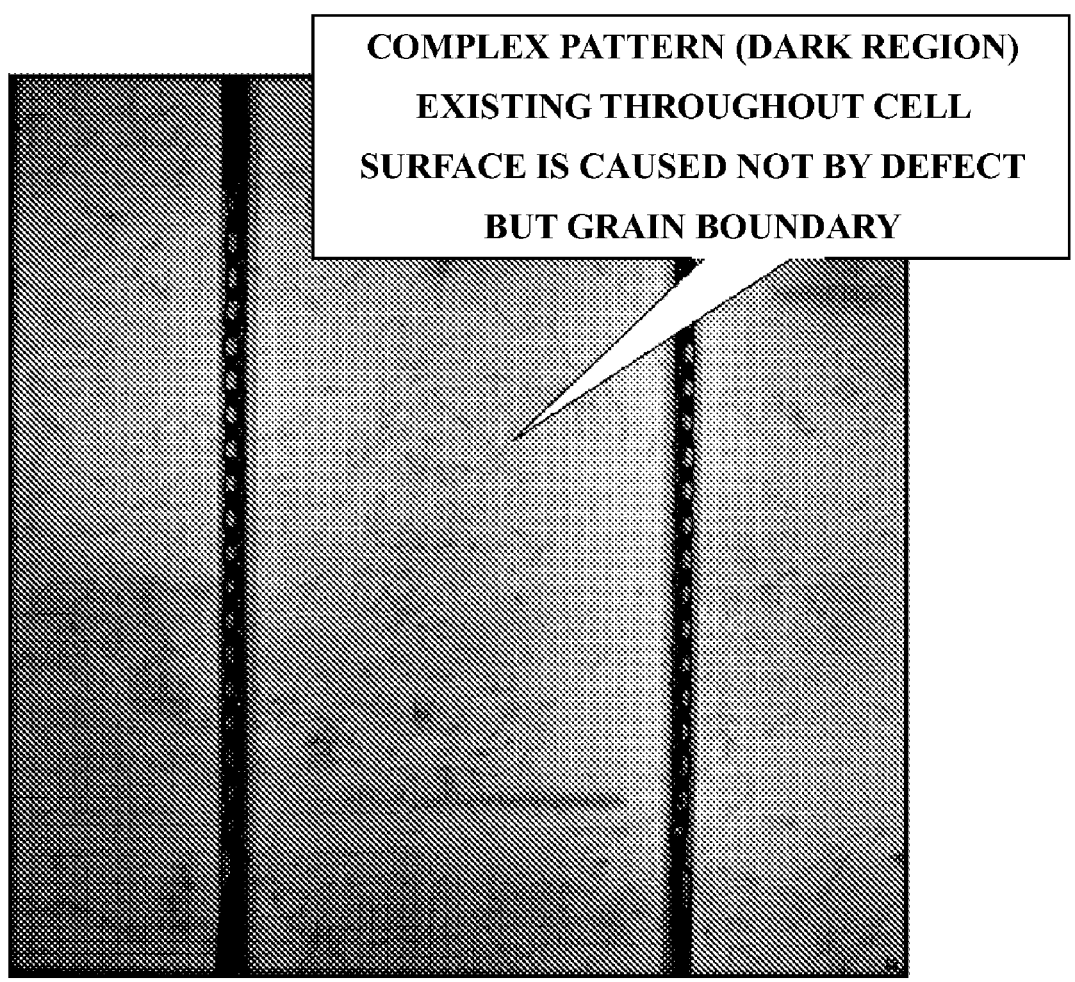
FIG. 12 is an exemplary image photographed from a polycrystalline silicon cell.
Figure 13:
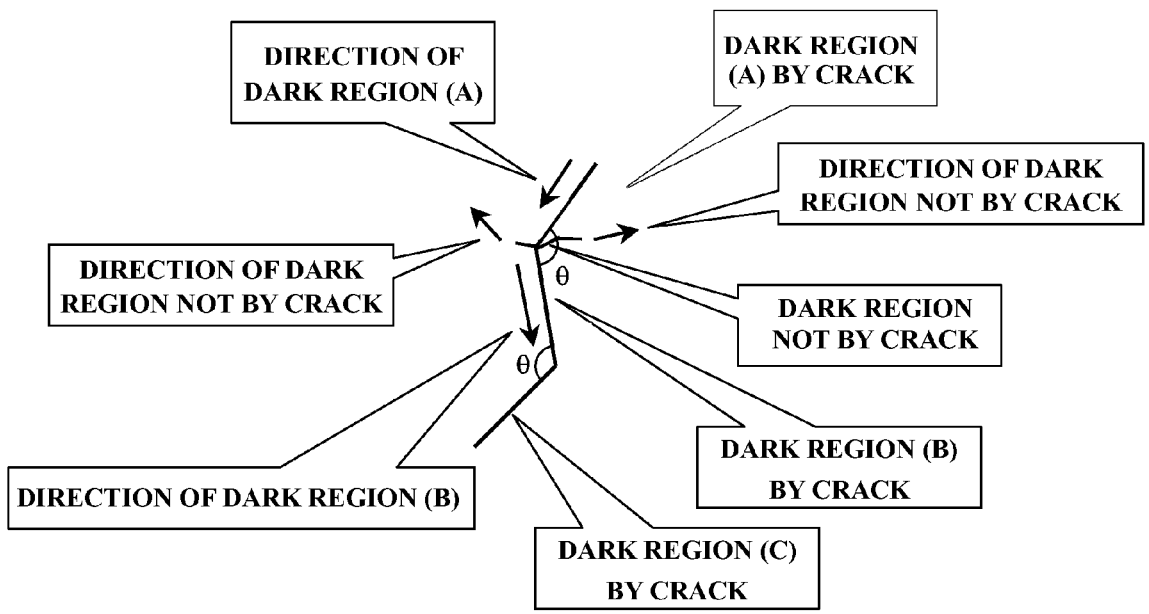
FIG. 13 is a view for explaining a method of determining a dark region of a photographed cell image as a crack.

FIG. 1 is a block diagram illustrating a schematic configuration of a photovoltaic device inspection apparatus according to an embodiment of the present invention, and FIGS. 2A to 2C are views illustrating the configuration of a camera position determination mechanism of the apparatus of the embodiment, where FIG. 2A is a plan view, FIG. 2B is a front view, and FIG. 2C is a right side view. FIG. 3 is a flowchart for explaining a method of inspecting a photovoltaic device according to the embodiment; FIG. 4 is a flowchart for specifically explaining a photographed image processing and quality (whether passed or not) determining process; and FIGS. 5A and 5B are exemplary images of a photovoltaic cell of the embodiment. FIG. 6 is a plan view illustrating photovoltaic cells, strings, and a matrix of a photovoltaic device as an inspection-object, and FIG. 7 is a sectional view illustrating the structure of a photovoltaic devices panel. FIG. 8 is a view illustrating a photovoltaic cell as an inspection-object of an inspection apparatus of the embodiment. FIGS. 9, 10, and 11 are views illustrating defects of photovoltaic cells as an inspection-object with different enhanced marks according to defect types. FIG. 12 is an exemplary electroluminescence (EL) image photographed from polycrystalline silicon cells. FIG. 13 is a view for explaining a method of determining a dark region of a photographed cell image as a crack.

<1> Inspection-Object (Photovoltaic Cell, Photovoltaic Devices Panel)

First, an explanation will be given of photovoltaic devices 100 as an inspection-object inspected by an inspection apparatus of the present embodiment.

As illustrated in the plan view of FIG. 6, a string 25 is formed by connecting a plural rectangular photovoltaic cells 28 in series through lead wires 29. In addition, strings 25 are connected to each other through plural lead wires to form a photovoltaic device panel as an inspection-object 100.

In the present invention, the photovoltaic devices as the inspection-object 100 may be formed of a single photovoltaic cell 28 only, or may be formed of a string 25 in which plural photovoltaic cells 28 are straightly connected, or may be a photovoltaic devices panel in which plural strings 25 are disposed in parallel rows to arrange photovoltaic cells 28 in a matrix format.

As illustrated in FIG. 7, the photovoltaic device panel as the inspection-object 100 has a sectional structure, in which the plural rows of strings 25 are sandwiched between a backside member 22 disposed at an upper side of the filling member 24 and a transparent cover glass 21 disposed at a lower side of the filling member 23, with strings 25 being disposed between the filling member 23 and 24.

The backside member 22 is made of, for example, polyethylene resin or the like. The filling members 23 and 24 are made of, for example, polyethylene vinyl acetate (EVA) resin. As described above, the string 25 is formed by connecting the photovoltaic cells 28 with lead wires 29 between electrodes 26 and 27.

The photovoltaic devices panel is formed by piling the aforementioned constructional members and performing a laminating process on the constructional members. The laminating process is performed by pressing the constructional members in a vacuum heated state for cross-linking of the EVA resin.

The rectangular photovoltaic cell 28 will now be described in detail. FIG. 8 is a plan view from the direction of a receiving optical side of the photovoltaic cell 28. In the photovoltaic cell 28, busbars are printed on a silicon semiconductor surface of a thin plate as electrodes for collecting electricity being taken out. In addition, fine conductors, which are called fingers, are printed on the silicon semiconductor surface vertically to the busbars for efficiently collecting electricity to the busbars.

Moreover, a kind of photovoltaic device, which is generally called a thin film-type photovoltaic device, may be employed as an inspection-object 100. An exemplary typical structure of the thin film-type photovoltaic device can be constructed by depositing a power generating element (including a transparent electrode, a semiconductor, and a backside electrode) on a transparent cover glass 21 disposed in the lower part of FIG. 7.

Such a thin film-type photovoltaic devices panel is formed through a laminating process into the above-described structure by disposing a glass at a lower side, covering the photovoltaic cells deposited on the glass with a filling member, and covering the filling member with a backside member.

The thin film-type photovoltaic devices panel as an inspection-object 100 replaces crystalline cells with the above-described power generating elements, and the basic sealing structure is identical to the photovoltaic devices panel formed of crystalline cells.

<2> Defects of Photovoltaic Cell

Defects of photovoltaic cells can be classified into several types according to the causes of the defects, and the defect types are then characterized by their shapes. In the present invention, defects are classified into "finger break", "crack", and "fragment". This is an exemplary classification. Other classifications may be used.

FIG. 9 illustrates an exemplary finger break which forms a dark region. In FIG. 9, plural horizontal fine lines indicate fingers. In the case of a finger break, a rectangular dark region is formed in the direction of the broken finger.

FIG. 10 illustrates exemplary cracks, which are linear defects formed by cracking. In regions M and N adjacent to busbars, a crack can be formed by thermal deformation when a lead wire is soldered on the busbar. A crack caused by thermal deformation is relatively small.

A crack may be caused by compression during a laminating process, or handling loads or impacts during transportation or during the module manufacturing process; such a crack may be formed in a region L as well as the regions M and N. This kind of crack may be relatively large as compared with the above-described crack caused by soldering. Since a semiconductor is hard and fragile, generally, such a crack has a simple shape, although the crack may have a bent portion.

FIG. 11 illustrates examples of fragments. A fragment means a regional defect having an arbitrary area, which is characterized by a crack formed at a side of a regional defect and forms a dark region. According to the split state of a semiconductor by a crack, the shape of a dark region varies. If the semiconductor is split down the length due to a crack as shown in a region C1 in the drawing, a dark region having an area is formed at a side of the crack opposite to a busbar. If a part of the semiconductor is completely removed, as shown in a region C2 of the drawing, light is not emitted from the removed part, and thus a dark region having an area is formed. If a part of the semiconductor is completely split although it is not completely removed as shown in a region C3 of the drawing, a dark region having an area is formed from a crack to an end of the semiconductor. The darkness of the above-described dark regions are usually uniform in the dark region. That is, it is rare that relatively bright and dark parts are complexly mixed in a dark region.

In a photographed image, a non-defective region can be shown as a dark region. FIG. 12 is an exemplary image photographed from a polycrystalline silicon cell. In the image, patterned dark regions which are distributed throughout the entire surface of the cell, and have complex shape, are not defective regions but boundaries of crystals. In determining whether to pass or not for a cell, non-defective dark regions should be distinguished from dark regions caused by defects. Therefore, various image processing techniques and determination references whether to pass or not are considered as described later.

<3> Configuration of Photovoltaic Device Inspection Apparatus of the Present Invention FIG. 1 is a block diagram illustrating a schematic configuration of a photovoltaic device inspection apparatus according to an embodiment of the present invention. In the embodiment, a control unit 10 is used to control the overall operations of the inspection apparatus and to determine whether a photovoltaic device passes inspection or not, and is configured by a personal computer. Programs or various types of data executed by the control unit 10 are stored in a memory 20. A reference data file 30 contains reference data for determining whether a photovoltaic device panel passes inspection or not.

Preset values are registered in the reference data file 30 according to the types of inspection-objects (cell/string/matrix, refer to FIG. 6). Examples of the preset values are as follows.

(1) Light emission conditions of photovoltaic cells
(2) Photovoltaic cell gap (camera shift pitch)
(3) The number of photovoltaic cells (vertical, horizontal) of string/matrix
(4) Preset information about dimensions of photovoltaic cells (busbar positions, corner chamfers, finger arrangements, DIP positions, etc.)

Dimensional information of photovoltaic cells may be set by a basic-type method of setting and filling in the screen (display), a setting method using graphic information, and a combination thereof. In the case of the setting method using graphic information, DXF and BMP format files are prepared as graphic information, and in the case of the above-described method of setting and filling in the screen, plural types can be selected for different cases such as case(A) where the number of busbar is "1", case(B) where the number of busbar is "2", case(C) where the number of busbar is "3", and so on.

(5) Image processing conditions
(6) Image photographing conditions
(7) Data according to defect types (characteristics of shapes, threshold values of length or area)

In the present invention, defects are classified into [finger break], [crack], and [fragment]. According to the above-described features of defects, a finger break is determined based on whether the shape of a dark region is rectangular in the direction of a finger. Since a crack appears in the form of a dark region having a straight line or bent-line shape, a crack is determined based on whether a dark region has a linear shape and a threshold of a length. A fragment is determined based on whether the area of a dark region is equal to or greater than a threshold value.

An input/output control unit 40 controls input/output devices such as a keyboard 400 through which instruction commands or determined results as to whether the device passes or not are input. A camera control unit 50 controls a photovoltaic device photographing camera 500 configured to photograph an image of an inspection-object 100 (photovoltaic devices panel). A display control unit 60 controls a display unit 600 configured to display a photographed image. A measurement current control unit 70 is a power means configured to apply a predetermined current (a predetermined forward current) to the inspection-object 100 (photovoltaic devices panel) through a probe 75. The probe 75 is used to apply a current to the photovoltaic devices panel. A position determination mechanism control unit 80 carries the camera 500 to a photographing position and determines the position of the camera 500 by controlling a camera position determination mechanism 800. A camera photographing unit including the camera position determination mechanism 800 is illustrated in detail in FIG. 2. Reference numeral 900 denotes an external memory device configured to store determined results of cells as to whether they passed or not. Among the above-described elements, an analyzing means 200 is comprised of the control unit 10, the memory 20, the reference data file 30, the input/output control unit 40, the display control unit 60, and the external memory device 900.

In the inspection apparatus of the present embodiment, the inspection-object 100 (photovoltaic devices panel) works as EL light source by applying a forward current to the photovoltaic devices panel from the measurement current control unit 70 through the probe 75 and the state of the EL light is photographed by camera 500. Since photovoltaic cells of the photovoltaic devices panel are sequentially photographed, the camera 500 is moved according to the positions of the photovoltaic cells by the camera position determination mechanism 800.

In a darkroom, the camera 500 photographs the inspection-object 100 emitting a weak EL light ray having a wavelength of 1,000 nm to 1,300 nm. Therefore, it is necessary to use a camera having high sensitivity to a weak light ray, such as the camera 500. In the present embodiment, a Si-CCD camera Model C9299-02 manufactured by Hamamatsu Photonics K. K. is employed as the camera 500.

Next, with reference to FIG. 2, explanations will be given on how the camera photographing unit 500 and the camera position determination mechanism 800 are configured and controlled. In FIG. 2, detailed structures of the camera photographing unit 500 (photovoltaic device photographing camera in the figure) including the camera position determination mechanism 800 are illustrated.

In the camera position determination mechanism 800, a transparent plate 812 made of a synthetic resin such as an acryl resin or glass is disposed at a flat upper surface 811 of a square box type darkroom 810. Except for the transparent plate 812, the dark room 810 is made of shading materials so as to shade darkroom 810. It is necessary to cover a gap between the transparent plate 812 and the inspection-object 100 with a shading member. In the case where the inspection-object 100 (photovoltaic devices) is placed on the upper surface 811 and then the upper surface 811 and the inspection-object 100 is entirely covered with a shading means, the upper surface 811 may be wholly formed by a transparent plate. The other four lateral surfaces and bottom surface are made of shading members. A pair of guide members 814 is provided at the upper surface 811 for guiding the inspection-object 100 during transporting.

The darkroom 810 is provided with the camera 500, and a Y axis guide part 830 for moving the camera 500 in the Y axial direction. A motor 832 is disposed at one end of the Y axis guide part 830. The camera 500 is moved forward or backward along the Y axial direction according to the rotation of the motor 832.

Both ends of the Y axis guide part 830 are supported by X axis guide parts 840, respectively. The Y axis guide part 830 can be moved forward or backward on the X axis guide parts along the X axial direction by a motor 842 and both-side timing belts 844.

In the aforementioned configuration, the X axis guide parts 840, the Y axis guide part 830, the motors 832 and 842, and the timing belts 844 constitute a driving mechanism for the camera 500. In the present embodiment, the X axis guide parts 840 and the Y axis guide part 830 are driven by the motors 832, 842 and ball screws. However, the driving method is not limited to the above-described embodiment. For example, other linear actuators can be used.

By controlling the rotations of the motors 832 and 842 of the driving mechanism, the camera 500 can be moved to an arbitrary position on the X-Y plane so as to make it possible to photograph any part of the inspection-object 100.

The inspection-object 100 (photovoltaic devices) may be a photovoltaic cell 28, a string 25 which is formed by straightly connecting plural photovoltaic cells 28 with lead wires as illustrated in FIG. 6, or a photovoltaic devices panel in which plural rows of strings 25 are disposed in parallel to arrange photovoltaic cells 28 in a matrix format. The camera 500 may photograph the photovoltaic cells one by one or group by group, or the photovoltaic devices panel at a time.

In the inspection-object 100 (photovoltaic devices), photovoltaic cells 28 are arranged in a row and electrically connected to form a string 25, and then such strings 25 are arranged in parallel so as to dispose the photovoltaic cells 28 in a matrix format in horizontal and vertical directions. As illustrated in FIG. 7, a transparent cover glass 21 is disposed at the lowermost side, an EVA (polyethylene vinyl acetate) resin 23 used as a filling member, photovoltaic cells 28, an EVA 24, and an upper backside member 22, formed of a resin, are piled above the lower transparent cover glass 21. Then, they are pressed in a heated vacuum state in a laminating apparatus to form a laminate structure by cross-linking of the EVA. The photovoltaic devices panel is carried out of the laminating apparatus and is then transported to the photovoltaic device inspection apparatus of the present invention via a conveyer. The photovoltaic devices panel is transported to an upper side of the dark room 810, guided between the guide members 814.

As illustrated in FIG. 2, the inspection-object 100 transported to the upper side of the darkroom 810 is positioned above the transparent plate 812 of the darkroom 810 with the transparent cover glass 21 facing downward, and the measurement current control unit 70 is connected to the inspection-object 100 through the probe 75. Since the inspection-object 100 is smaller than the transparent plate 812, light rays can enter the darkroom 810, and thus the upper surface of the darkroom 810 is entirely covered with a shading means (not shown) from the top side of the inspection-object 100. Or, it is necessary to cover the gap between the transparent plate 812 and the inspection-object 100 with a proper shading member.

It is described above that the shading means covers the entire upper surface of the darkroom 810. However, in the case of the photovoltaic devices panel, since the backside member 22 disposed at the backside is made of an opaque resin, light can be shaded. Moreover, the upper surface 811 of the darkroom 810 is configured of a shading member except for the transparent plate 812. In the case where the inspection-object 100 is larger than the transparent plate 812 and the inspection-object 100 covers the entire transparent plate 812, then the shading means is not necessary.

In the case where the inspection-object 100 is smaller than the transparent plate 812, because light can enter the darkroom 810 through a gap, the inspection-object 100 shall be covered with a shading means. At least, the shading means covers a frame-shaped gap between the transparent plate 812 and the inspection-object 100. Therefore, the shading means must be sized at least to cover the gap.

In the present embodiment, a special darkroom is not necessary for inspecting photovoltaic devices. That is, photovoltaic devices may be inspected by placing the photovoltaic devices in the apparatus having the simple mechanism as shown in FIG. 2. Moreover, in the present embodiment, the inspection apparatus is provided with only the camera position determination mechanism as shown in FIG. 2 and a computer system, and thus the following advantages can be attained.

During the manufacturing process of a photovoltaic devices panel, for example a laminating process of a photovoltaic devices panel, generally, the photovoltaic devices panel is transported with its glass surface facing downward. In the inspection apparatus, the photovoltaic devices can be placed at the upper surface 811 of the darkroom with the receiving optical side of the photovoltaic devices facing downward, and thus a turning-over operation is unnecessary. Therefore, during a manufacturing process, a photovoltaic devices panel can be easily placed at the inspection apparatus.

<4> Inspection Flow of Photovoltaic Devices Panel

The analyzing means 200 photographs photovoltaic devices panel and inspects the photovoltaic device panel for defects according to the flowchart of FIG. 3.

First, in step S1, the position of a photovoltaic devices panel (inspection-object 100) is positioned and placed at the upper surface 811 of the darkroom 810. Next, in step S3, the probe 75 is connected to a terminal part of the photovoltaic devices panel so that a current can be applied from the measurement current control unit 70 to the photovoltaic devices panel.

In step S5, the control unit 10 controls the position determination mechanism control unit 80 so as to place the camera 500 at an initial photographing position of the photovoltaic devices panel. In step S7, the measurement current control unit 70 is controlled to apply a predetermined forward current to the photovoltaic devices panel (inspection-object 100) for EL emission of the photovoltaic devices panel. Light emission conditions (current values and current applying times) are preset according to inspection-objects and are registered in the reference data file 30. In the present embodiment, the light emitting condition is configured such that three light emission conditions are set to one photographing condition. The reason for this is that excessive EL emission or insufficient EL emission can occur according to cell characteristics if only a single condition is used.

Because plural light emission conditions are set, if it is determined that photographed results are insufficient during performing a photographed image process, light emission conditions can be changed according to the situation, and the procedure can go back to step S7. In the following description, this "go-back" or return procedure will be omitted.

In step S10, the control unit 10 controls the camera control unit 50 to photograph a photovoltaic cell 28 emitting EL light by using the camera 500; the photographed image is taken in the camera control unit 50 and is stored in, for example, predetermined regions of the memory 20 and the external memory device 900.

In step S12, the display control unit 60 is controlled to read the original photographed image from the memory 20 and display the photographed image on the display unit 600. In step S50, the analyzing means 200 performs the photographed image process for analyzing the photographed image. In step S16, according to the results of the image processes in step S50, regions of the image determined as defects are enhanced and the image is displayed on the display unit 600 by the display control unit 60.

S18 is a step of being manually inspected by an inspector (manual determination process) by using the enhanced image, which will be described in more detail in section <7>.

In step S20, the control unit 10 of the analyzing means 200 stores the determined results of the cell in, for example, the external memory device 900.

In step S22, a count-up process is performed to proceed the sequence number to the next one, which is allocated for all photovoltaic cells 28 of the photovoltaic devices panel (inspection-object 100). In step S24, the count-up sequence number is checked so as to determine whether photographing and determination are completed for all the photovoltaic cells 28 of the photovoltaic devices panel (inspection-object 100). If it is determined that photographing and determination are not completed for all the photovoltaic cells 28, the procedure goes to step S30 to control the camera position determination mechanism 800 using the position determination mechanism control unit 80 so as to move the camera 500 to a photographing position of the next photovoltaic cell, and then the procedure goes back to step S7 for performing photographing and determination on the next cell.

Meanwhile, in step S24, if it is determined that photographing and determination are completed for all the photovoltaic cells 28, the procedure goes to step S26, and overall determination is performed as described in section <6>. Thereafter, other inspection points such as gaps between photovoltaic cells of the photovoltaic devices panel are checked to determine whether the photovoltaic devices panel is wholly passed or not, and the determined results are stored in, for example, a predetermined region of the external memory device 900. In this way, an overall determination of a sheet of photovoltaic devices panel is completed.

<5> Detailed Description of Photographed Image Process; S50

Next, with reference to FIG. 4, photographed image process step S50 will be described in detail. In the image process, an image of a photovoltaic cell 28 read out from the memory 20, and then a region (dark region) where light intensity is weak is extracted from the image of the photovoltaic cell 28. Next, the dark region (or shape) is image-processed according to defect types of photovoltaic cells as shown in FIGS. 9, 10, and 11. Image process conditions are registered in the reference data file 30. Then, the following processes are sequentially performed.

In step S52, the analyzing means 200 performs a scaling process on the image data of a sheet of photovoltaic cell 28 read from the memory 20. According to the features of the photovoltaic cell 28, the total amount of light emission varies across the photovoltaic cell 28. In the scaling process, the most bright part is normalized to a predetermined lightness value, and the brightness of the whole image is adjusted for making it possible to compare brightness under a predetermined condition.

In step S54, regions of the photovoltaic cell 28 are extracted. In this process, the outline of the photovoltaic cell 28 is automatically calculated with reference to cell dimension information registered in the reference data file 30. Even if the photovoltaic cell 28 is not correctly placed in respect to the position and angle, the outline of the photovoltaic cell 28 can be precisely calculated by this process, and the angle of the photovoltaic cell 28 can be corrected by this process. At this time, arrangement of adjacent photovoltaic cells can be checked by consecutively photographing the adjacent photovoltaic cells, so as to determine whether there is a proper gap or not.

In step S56, a busbar removing process is performed to remove busbar regions from the photographed image for determining whether the cell passed or not. The regions of busbars of the photovoltaic cell 28 are automatically calculated with reference to cell dimension information previously stored in the reference data file 30, and then the busbar regions are removed so as to determine whether or not the photovoltaic cell 28 passed without the busbar regions. In this process, even if the position or angle of the photovoltaic cell 28 is not correct, the busbar regions can be exactly calculated.

In step S58, a shading process is performed. According to the characteristics of a lens of the camera 500, basically, the center region of the image may be brighter than the peripheral region. Thus, this brightness difference caused by the lens characteristics of the camera 500 is compensated by this process.

Before determining defect, regions of the image are classified into bright and dark regions. Whether a region is a dark region or not is determined by using a decreasing ratio of brightness to a peripheral region as a threshold value. An exemplary method of distinguishing bright and dark regions will be hereinafter described.

The photographed image is divided into small sections having a predetermined size, and the brightness average value of the small sections is calculated. Then, a small section where bright and dark parts are mixed is searched for, and the brightness average of the searched small section is calculated. Instead, a brightness average of plural sections having similar brightness values may be calculated. By this brightness average calculation, the brightness difference of a region where bright and dark parts are complexly mixed is reduced so that boundaries of brightness and darkness are eliminated. By using the brightness average value calculated at this time, a threshold value of brightness and darkness is determined. For example, the brightness average value or a value slightly smaller than the brightness average value (darker value) may be set as a brightness threshold value. Then, small sections having brightness values smaller than the brightness threshold value are determined as dark regions.

That is, in the case of a uniformly dark region (i.e., a region suspected to be a fragment region), after the above-described averaging of small sections, since the brightness average value of a small section corresponding to the dark region becomes smaller (dark), then the corresponding small section can be determined as a dark region.

In addition, there may be a case where a uniformly dark region and a peripheral bright region thereof are included in a small section, for example, the small section has partially bright part and the other part is dark. In this case, if the brightness average value of the small section is greater than the brightness threshold value, the small section is determined as a bright region, and if the brightness average value is smaller than the brightness threshold value, the small section is determined as a dark region. In this way, the photographed image can be divided into [bright region] and [dark region] by using the brightness average value of a small section where bright and dark parts are complexly mixed as a brightness threshold value.

Other methods can be used to distinguish bright and dark regions, as well as the method of distinguishing bright and dark regions by dividing the photographed image into small sections. For example, in the case of a digital image, a predetermined number of pixels linearly arranged can be defined as a small section, or plural pixels forming a predetermined area can be defined as a small section, and then the same process as described above can be performed. For instance, a section where bright and dark parts are complexly mixed can be selected for watching, and the brightness average value of the section can be set as a brightness threshold value. In addition, the size of a small section defined for calculating a brightness threshold value may be different from the size of small sections for distinguishing bright and dark regions. For example, the size of small sections for distinguishing bright and dark regions may be smaller than the size of a small section defined for calculating a brightness threshold value.

In the case where the brightness values of plural photovoltaic cells are adjusted evenly by a proper scaling process or shading process, the same brightness threshold value can be used for inspecting the plural photovoltaic cells.

Therefore, the bright and dark regions of the image can be enhanced by binarization, for example, using a method of setting [bright region] as 0 and [dark region] as 1.

In this way, the image photographed by the camera 500 is divided into bright and dark regions with the units of small sections. However, although the photographed image is divided into bright and dark regions according to its brightness, a defective region of the photographed image is not yet determined. Determination of a defective region is performed as follows.

First, defects are classified into predetermined types. Here, defects are classified into three types: [fragment], [finger break], and [crack]. These three types are exemplary types, and other types can be included. Threshold values of shapes, lengths, and areas of the respective defect types are previously stored in the reference data file 30.

In step 60, one of the defect types, [fragment], is detected. This fragment detection process is performed by extracting a dark region having an area greater than a threshold value as a fragment from dark regions having areas that are located around the periphery of a photovoltaic cell. Generally, a dark region caused by a fragment (defect) is uniformly dark as compared with a neighboring bright region, as shown in FIG. 11. However, in a dark region not caused by a defect, bright and dark parts are complexly mixed, as shown in FIG. 12. This region is almost determined as a bright region, as understood from the above-described method of calculating a threshold value. Although such a region may be determined as a dark region according to the size of small sections, in this case, because the area of the region is smaller than an area threshold value, the region is not determined as a fragment.

After the fragment determination, defective regions of the fragment determined image can be enhanced and displayed in step S16 through a binarization process, such as a process of setting a dark region of a fragment as 1 and bright regions around the dark region as 0. FIG. 11 illustrates an exemplary display enhanced fragment. A dark region determined as a [fragment] may be displayed with a color corresponding to the defect type (fragment).

In the case where a defect is automatically determined using the analyzing means 200, bright and dark regions may be included in image data in the form of binary data, and it may not be necessary to display the image in a digital format. However, the image can be displayed on a display for monitoring the progress state of the determination by watching.

In step S62, a finger break detection process is performed. In this process, if a dark region of the cell image has an area equal to or greater than a predetermined value, the dark region is detected as a finger break. In this process, a finger break can be detected by performing the same brightness averaging so that it is now performed in the fragment detection process, and extracting a uniform dark region. A dark region caused by a finger break generally has a rectangular shape in the direction of the finger. Therefore, with reference to finger direction information stored in the reference data file 30, a dark region having a shape similar to a rectangle and being consistent with the finger direction is determined as a finger break.

The bright and dark regions of the image can be enhanced by setting bright regions as 0 and dark regions as 1. In this way, defective regions of the determination image can be enhanced and displayed in step S16. FIG. 9 illustrates an enhanced finger break. A dark region determined as a finger break may be displayed with a color corresponding to the defect type (finger break) that is different from the color used for a fragment. For efficient detecting of a finger break, it is desirable that the above-described small sections are set to have a square shape, and a side of the square is set to be smaller than the distance between adjacent fingers.

In step S64, a crack detection process is performed. In this process, dark regions are detected according to the above-described method of distinguishing bright and dark regions. Then, except a dark region of a finger break, a dark region having a linear shape equal to or longer than a predetermined length is detected as a crack. Generally, a dark region caused by a crack has a bent linear shape and is a relatively simple shape. Hereinafter, a method of determining a crack will be explained with reference to FIG. 13.

A dark region caused by a crack has a shape formed by a combination of simple segments as described below. In the crack detection process, a dark part having bent-linear shape (A), (B), and (C) caused by a crack are recognized as a single crack, and the length of the crack is calculated as the sum of lengths of the dark segments (A), (B), and (C). In addition, angles θ of bent parts are obtuse angles equal to or greater than 90°. In the case of a dark region caused by only a crack, only based on whether segments are connected at joints, it can be determined whether the segments are included in the same dark region.

As explained in <2> Defects of Photovoltaic Cell, a dark region not caused by a crack can exist in a photographed image. A representative example is a dark region caused by an internal factor, such as a grain boundary. If such a dark region is overlapped with a joint point of a dark region caused by a crack, it is difficult to recognize the crack only by checking the joint part of the line. Although such a dark region can be reduced by increasing the temperature, the temperature increasing method is not used because it takes much time. Instead, the following method is employed.

Since a dark region has a relatively simple shape (the angle of a joint point is obtuse) as shown in FIG. 13, it can be considered that directions of segments are not largely different. However, since a dark region not caused by a crack has a random direction, there is a low possibility that the direction of such a dark region is consistent with the direction of a crack.

Therefore, in the case of determining the next dark region (the next segment) connected to a joint point, a dark region (segment) having a direction similar to that of the previous dark region (segment) is determined as the next dark region (segment). In this way, a crack can be fully recognized. In addition, a length threshold value can be used.

In the case of generating an enhanced image for enhancing and displaying determined results, a dark region determined as a crack and a neighboring bright region are displayed in binary format. Colors can be used for dark regions according to the types of defects for displaying. In this way, display of step S16 can be done.

As explained in <2> Defects of Photovoltaic Cell, a dark region not caused by a crack can exist in a photographed image. In such a dark region, bright and dark regions are complexly mixed, and basically, the dark region can be treated by using the above-described brightness distribution averaging method. However, all regions darker than a brightness threshold value can be determined as dark regions. In addition, since a crack is determined based on whether the crack has a length equal to or longer than a predetermined length (length threshold value), if the length threshold value is lowered, a dark region not caused by a crack can be determined as a dark region caused by a crack. However, since there can be a problematic small crack, it is not preferable to increase the length threshold value. Therefore, the following references are used for determining a crack.

As crack determination references, two kinds of references corresponding to regional characteristics of a photovoltaic cell are prepared. As illustrated in FIG. 10, a photovoltaic cell is divided into periphery regions of busbar (regions M and N) and other regions L. A first determination reference is prepared mainly for cracks caused by compression during a laminating process, or handling loads, or impacts during transportation, or during the module manufacturing process. Such cracks can be formed in all regions M, N, and L. If a length threshold value of such a crack is small, a dark region not caused by a crack can be determined as a crack. Particularly, in the region L, noises may be generated as a result of such incorrect determination of cracks. Therefore, it is preferable that the length threshold value is sufficiently large for detecting relatively large cracks exactly.

A second determination reference is prepared for the regions M and N. In the regions, relatively small cracks are generally formed when lead wires are soldered onto the busbars. Therefore, a relatively small length threshold value is set for the regions M and N for detecting relatively small cracks.

By preparing the first determination reference for a long linear dark region caused by a crack, a crack can be exactly detected, and detection of a dark region not caused by a crack can be prevented. In addition, by preparing the second determination reference for a short linear dark region caused by a crack, even a small crack can be detected.

Typically, the regions M and N have the same size. However, the regions M and N may have different sizes. In addition, different crack length threshold values can be used for the regions M and N.

In the above-described automatic determination of photovoltaic cells, the existence of fragment, finger break, and crack are determined. In the determination, dark regions not determined as defects due to their small sizes (areas) or lengths may be treated as bright regions so as to reduce noise.

In the automatic determination of step S66, the sizes (areas, lengths) and numbers of detected fragments, finger breaks, and cracks are compared with predetermined threshold values so as to determine whether the photovoltaic cell passes or not. Next, in step S68, the determination results are output.

A photovoltaic cell not having such defects is determined as a non-defective cell. If defects are detected, cells are graded based on detected information about fragment, finger break, and crack.

The grading is conducted based on the following items. (1) Sum of areas of detected fragments, (2) sum of areas of detected finger breaks, and (3) sum of lengths of detected cracks are compared with predetermined threshold values to give grades to the each items ((1), (2) and (3)). For example, five grades of A, B, C, D, and E are given, where A means the highest grade and E means the lowest grade. A cell determined as a defective cell is given E grade in the automatic determination. If the grade of a cell is equal to or lower than a predetermined grade, it is determined as defective. The predetermined grade can be varied. For example, determination references can be varied. If the photovoltaic cell has a [fragment] equal to or greater than a predetermined area or a [crack] equal to or longer than a predetermined length, the photovoltaic devices can be determined as a defective one based on the fact that the performance of the photovoltaic cell decreases intensely in the near future.

<6> Overall Determination; S26

If an inspection-object is a photovoltaic cell, a determined result of the photovoltaic cell is an overall determined result of the product (photovoltaic cell). However, if an inspection-object is a string or matrix, overall determination of a product is performed as follows.

Overall determination of the photovoltaic devices is performed based on the determination reference of each photovoltaic cell and the number of photovoltaic cells counted according to each grade. For example, if the number of photovoltaic cells having grades equal to or lower than a preset grade is equal to or greater than a preset number, the product is determined to be defective. For instance, the product may be determined to be defective if the product is in any one of the following three cases: the number of photovoltaic cells having grade C or lower grades is five or more; the number of photovoltaic cells having grade D or lower grades is three or more; and the number of photovoltaic cells having grade E is one or more.

<7> Manual Determination by Inspector; S18

In the photovoltaic devices inspection apparatus of the present embodiment, processes can be automatically performed from photographing to defect determination. However, for example, if a photographed image is determined to be problematic, the photographed image and the dark region can be displayed on a display unit in a state where the dark regions of the image are enhanced. Then, after stopping the automatic determination operation of the photovoltaic device inspection apparatus, an inspector can manually determine the image displayed on the display unit (refer to step S18 of FIG. 3). The manual determination is performed by an inspector as follows.

In step S18 of FIG. 3, an inspector determines whether passed or not while watching the enhanced image, and the inspect inputs the determined result through the keyboard 400. In the case where the display unit 600 is a touch panel, the inspector can input the determined result by touching the displaying panel of display unit 600.

In the inspection apparatus of the present embodiment, an inspector can set a determination function [effective/non-effective], an automatic determination function [effective/non-effective], and a manual determination function [effective/non-effective], so as to determine whether the product passed or not while checking the photographed image of the product displayed on the display unit. In the case where an inspector inspects a string or matrix product, when all photovoltaic cells of the product are determined to have passed or not, the inspector may push a product determination completion button to finish inspection of the product (photovoltaic device panel).

<8> Enhancing and Processing of Image; S16

According to the present embodiment, as examples of determined images in which defective regions are enhanced in step S16, a finger break example is illustrated in FIG. 9, a crack example is illustrated in FIG. 10, and a fragment example is illustrated in FIG. 11. In the drawings, defective regions and the other regions are displayed after binarization. The other regions are displayed as [brightness] regions.

Another display method is shown in FIGS. 5A and 5B. FIG. 5A illustrates an original photograph image. FIG. 5B illustrates a defect-enhanced image overlapped with the original photograph image of FIG. 5A. Owing to this, during a manual determination, an inspector can determine while comparing the two images, so that determination whether passed or not can be made on the photograph image more easily and surely. In addition, threshold values of automatic determination can be varied, enabling more exact automatic determination.

As many apparently widely different embodiments of the present invention can be made without departing from the spirit and scope thereof, it is to be understood that the invention is not limited to the specific embodiments thereof except as defined in the appended claims.

What is claimed is:

1. A photovoltaic devices inspection apparatus for determining whether a photovoltaic cell of photovoltaic devices is defective or non-defective, the photovoltaic devices inspection apparatus comprising:
   a power supply configured to apply a forward current to a photovoltaic cell as an inspection-object;
   a camera configured to photograph the photovoltaic cell when the photovoltaic cell emits light in response to a current applied from the power supply; and
   an analyzer configured to analyze an image photographed from the photovoltaic cell by using the camera,
   wherein the analyzer:
   (a) calculates a threshold value of brightness and darkness based on an average brightness of a region of the photographed image where bright and dark parts are mixed in respect to the photographed image of the photovoltaic cell by using the camera,
   (b) divides the photographed image into bright and dark regions based on the threshold value of brightness and darkness and displays the bright and dark regions,
   (c) determines existence of a defect and a defect type for each photovoltaic cell of the photovoltaic device by previously classifying and registering the defect types and comparing a shape of the dark region with the preregistered threshold value of the defect type,
   (d) enhances the bright and dark regions by binarizing and displaying the bright and dark regions, and
   (e) determines existence of a defect for each photovoltaic cell of the photovoltaic devices.

2. The photovoltaic devices inspection apparatus according to claim 1,
   wherein
   the analyzer:
   (a) calculates and determines a threshold value of brightness and darkness where the threshold value of brightness and darkness is a predetermined degree darker than the average brightness of a predetermined small section of the photographed image where bright and dark parts are mixed in respect to the photographed image of the photovoltaic cell,
   (b) divides the photographed image into bright and dark regions per said small section based on the threshold value of brightness and darkness,
   (c) enhances the bright and dark regions by binarizing and displaying the bright and dark regions, and
   (d) determines existence of a defect for each photovoltaic cell of the photovoltaic devices.

3. The photovoltaic devices inspection apparatus according to claim 2, wherein the analyzer determines existence of a particular defect only for a predetermined region of the photovoltaic cell and does not determine existence of the particular defect for the other region of the photovoltaic cell.

4. The photovoltaic devices inspection apparatus according to claim 3, wherein the region determined as a defect is displayed with a color according to a type of the defect.

5. The photovoltaic devices inspection apparatus according to claim 2, wherein the region determined as a defect is displayed with a color according to a type of the defect.

6. The photovoltaic devices inspection apparatus according to claim 1, further comprising a display configured to display an image visibly by binarizing the region determined as a defect and the other region.

7. The photovoltaic devices inspection apparatus according to claim 6, wherein the region determined as a defect is displayed on the display in a state that the region determined as a defect is overlapped with the photographed image.

8. The photovoltaic devices inspection apparatus according to claim 7, wherein the region determined as a defect is displayed with a color according to a type of the defect.

9. The photovoltaic devices inspection apparatus according to claim 6, wherein the region determined as a defect is displayed with a color according to a type of the defect.

10. The photovoltaic devices inspection apparatus according to claim 1, wherein the camera consecutively photographs plural photovoltaic cells, and the analyzer determines whether the adjacent photovoltaic cells are properly arranged based on photographed images of the photovoltaic cells.

11. The photovoltaic devices inspection apparatus according to claim 1, wherein the analyzer determines existence of a particular defect only for a predetermined region of the photovoltaic cell and does not determine existence of the particular defect for the other region of the photovoltaic cell.

12. The photovoltaic devices inspection apparatus according to claim 11, wherein the region determined as a defect is displayed with a color according to a type of the defect.

13. The photovoltaic devices inspection apparatus according to claim 1, wherein the region determined as a defect is displayed with a color according to a type of the defect.

14. A method of determining a defect in photovoltaic devices, the method comprising steps of:
   applying a forward current from a power supply to a photovoltaic cell of a photovoltaic devices as an inspection-object;
   photographing light emitted from each photovoltaic cell by using a camera when the photovoltaic cell emits light in response to the applied current; and
   calculating a threshold value by an analyzer based on an average brightness of a region of the photographed image where bright and dark parts are mixed in respect to the photographed image of the photovoltaic cell by using the camera; and
   dividing the photographed image into bright and dark regions based on the threshold value of brightness and darkness, enhancing the bright and dark regions by binarizing and displaying the bright and dark regions, and determining existence of a defect for each photovoltaic cell of the photovoltaic devices by analyzer, where said analyzer
(a) determines existence of a defect and type of a defect by previously classifying and registering the defect types and comparing a shape of the dark region with the registered defect types, and
(b) enhances a region determined as a defect by binarizing and displaying the region determined as a defect and the other region.

15. The method of determining a defect in photovoltaic devices according to claim 14, wherein existence of a particular defect is determined only for a predetermined region of the photovoltaic cell, and the existence of the particular defect is not determined for the other region of the photovoltaic cell.

16. The method of determining a defect in photovoltaic devices according to claim 14, wherein plural photovoltaic cells are consecutively photographed, and are determined whether the adjacent photovoltaic cells are properly arranged based on photographed images of the photovoltaic cells.

17. The method of determining a defect in photovoltaic devices according to claim 14, wherein the region determined as a defect and the other region are binarized and displayed visibly as an image.

18. The method of determining a defect in photovoltaic devices according to claim 14, wherein the image formed by binarizing the region determined as a defect and the other region is displayed together with the photographed image of the photovoltaic cell.

* * * * *